United States Patent [19]

Collington et al.

[11] Patent Number: 4,847,370

[45] Date of Patent: Jul. 11, 1989

[54] CYCLOPENTYL ETHERS AND THEIR PREPARATION AND PHARMACEUTICAL FORMULATION

[75] Inventors: Eric W. Collington, Knebworth; Harry Finch, Letchworth; Duncan B. Judd; James D. Meadows, both of Ware, all of England

[73] Assignee: Glaxo Group Limited, London, England

[21] Appl. No.: 110,796

[22] Filed: Oct. 21, 1987

[30] Foreign Application Priority Data

Oct. 22, 1986 [GB] United Kingdom ............... 8625322

[51] Int. Cl.[4] .................. A61K 31/55; A61K 31/557; C07D 223/00
[52] U.S. Cl. .................... 536/103; 536/46; 514/925; 568/367; 568/379
[58] Field of Search ............. 536/103, 46; 514/212, 514/613, 708, 925, 58; 568/379, 367

[56] References Cited

U.S. PATENT DOCUMENTS

| | | | |
|---|---|---|---|
| 4,028,419 | 6/1977 | Nelson | 568/379 |
| 4,088,691 | 5/1978 | Nelson | 568/379 |
| 4,088,692 | 5/1978 | Nelson | 568/379 |
| 4,088,693 | 5/1978 | Nelson | 568/379 |
| 4,088,694 | 5/1978 | Nelson | 568/379 |
| 4,132,738 | 1/1979 | Kluender et al. | 568/367 |
| 4,206,151 | 6/1980 | Grudzinskas | 568/367 |
| 4,447,428 | 5/1984 | Collington et al. | 514/212 |

FOREIGN PATENT DOCUMENTS

2174702 11/1986 United Kingdom .

OTHER PUBLICATIONS

T. K. Schaaf et al., Journal of Medicinal Chemistry, 1981, vol. 24, No. 11, pp. 1352–1359.
Medline Computer Generated Abstract of Arzneimittelforshung, vol. 35, pp. 839–843 (1985) by Shriver et al.

*Primary Examiner*—Ronald W. Griffin
*Attorney, Agent, or Firm*—Bernard, Rothwell & Brown

[57] ABSTRACT

Compounds are described of formula

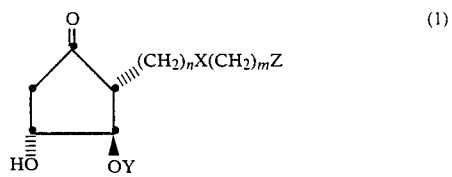

(1)

wherein
n is 1 or 2;
m is 2–5 and X is —CH=CH— or —CH$_2$—CH$_2$—; or m is 1–4 and x is —CH=C=CH—;
Z is —CH$_2$OH, —CHO or —CONHR$^1$ [where R$^1$ is a hydrogen atom or C$_{1-4}$ alkyl, aryl, —COR$^2$ (where R$^2$ is a hydrogen atom or a C$_{1-4}$ alkyl or aryl group) or —SO$_2$R$^3$ (where R$^3$ is a C$_{1-4}$ alkyl or aryl group)];
Y is substituted or unsubstituted 3-phenoxy-2-hydroxypropyl.

These compounds inhibit gastric acid secretion and provide gastrointestinal cytoprotection, and may be formulated for use in the treatment of ulcers.

10 Claims, No Drawings

CYCLOPENTYL ETHERS AND THEIR PREPARATION AND PHARMACEUTICAL FORMULATION

Prostaglandin E$_2$ is a naturally occurring substance which has many physiological actions. For example, it inhibits gastric acid secretion and provides gastrointestinal cytoprotection, lowers blood pressure, stimulates and relaxes smooth muscle, inhibits platelet aggregation and inhibits lipolysis.

Synthetic PGE$_2$ analogues offer the possibility of different potency, longer duration of activity and increased selectivity of action and are therefore of considerable interest.

We have now found a new group of cyclopentyl ethers that have PGE$_2$-type activity. Compounds in this class have a particularly useful profile of biological action. In particular they have shown high potency and improved selectivity as regards the inhibition of gastric acid secretion and gastrointestinal cytoprotection and are therefore of interest in the treatment of ulcers. Compounds of the invention also have a lipid lowering action and are of interest in the treatment of clinical conditions in which the underlying aetiology is associated with lipia imbalance or hyperlipidemia.

The invention thus provides compounds of the general formula (1)

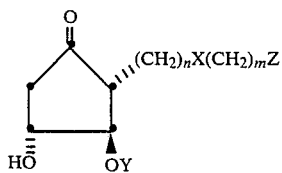
(1)

wherein
n is 1 or 2;
m is 2–5 and X is cis or trans —CH=CH— or —CH$_2$—CH$_2$—; or m is 1–4 and X is —CH=C=CH—;
Z is —CH$_2$OH, —CHO or —CONHR$^1$ [where R$^1$ is a hydrogen atom or C$_{1-4}$ alkyl, aryl, —COR$^2$ (where R$^2$ is a hydrogen atom or a C$_{1-4}$ alkyl or aryl group) or —SO$_2$R$^3$ (where R$^3$ is a C$_{1-4}$ alkyl or aryl group)];

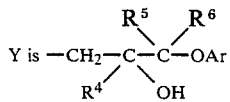

where R$^4$, R$^5$ and R$^6$ is each a hydrogen atom or a methyl group and at least one is a hydrogen atom; and
Ar is a phenyl group (optionally substituted by one or two C$_{1-4}$ alkyl, C$_{1-4}$ alkoxy, C$_{1-4}$ alkylthio, C$_{1-4}$ alkylsulphinyl, C$_{1-4}$ alkylsulphonyl, halogen or trifluoromethyl groups); and complexes (e.g. cyclodextrin complexes) thereof.

The structural formula herein are to be understood to include the enantiomers of each of the compounds concerned as well as mixtures of the enantiomers including racemates.

In general, the compounds of formula (1) in which the carbon atom carrying the group —(CH$_2$)$_n$X(CH$_2$)$_m$Z and/or the carbon atom in the group Y carrying the —OH group (particularly the former) are in the R-configuration and mixtures containing such isomers are preferred.

The term 'alkyl' as a group or part of a group within the definition of the compounds of formula (1) is intended to cover straight or branched chain moieties and may be, for example, a methyl, ethyl, n-propyl, i-propyl, n-butyl, s-butyl or t-butyl group. The term 'halogen' means fluorine, chlorine, bromine or iodine.

The aryl group referred to above in the definition of Z may be, for example, phenyl.

In compounds where X is —CH=CH— or —CH$_2$—CH$_2$—, m is preferably 3 when n is 1, and m is preferably 2 or 4 when n is 2. When X is —CH=C=CH—, m is preferably 2 and n is 1, and m is preferably 1 or 3 when n is 2.

When X is —CH=CH— it is preferably cis —CH=CH—.

When the group Z is —CONHR$^1$, R$^1$ may be, for example, a hydrogen atom or methyl, ethyl, phenyl, —COR$^2$ (where R$^2$ is a methyl or phenyl group) or —SO$_2$R$^3$ (where R$^3$ is a methyl or phenyl group).

Particular examples of the group Z include —CH$_2$OH, —CHO, —CONH$_2$, —CONHCH$_3$, —CONHCOCH$_3$, CONHSO$_2$CH$_3$ and

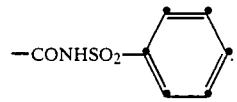

In the group Y, R$^5$ and R$^6$ are preferably hydrogen atoms.

When the Ar group is a substituted phenyl group, the substituent may be in the meta, ortho or para positions and may be for example methyl, ethyl, propyl, butyl, methoxy, ethoxy, propoxy, butoxy, methylthio, methylsulphinyl, methylsulphonyl, fluoro, chloro, bromo or trifluoromethyl. Preferably, only a single substituent is present, particularly at the para-position. In general, Ar is preferably phenyl or phenyl substituted by halogen, particularly fluoro or chloro.

The preferences indicated above apply both separately and in combination with one or more of the other stated preferences.

A preferred group of compounds of the invention are compounds of formula (1) in which:
X is —CH=CH— or —CH$_2$CH$_2$— and n is 1 and m is 3 or n is 2 and m is 2 or 4, or X is —CH=C=CH— and n is 1 and m is 2 or n is 2 and m is 1 or 3;
Z is —CH$_2$OH, —CHO, —CONH$_2$, —CONHCH$_3$, —CONHCOCH$_3$, —CONHSO$_2$CH$_3$ or

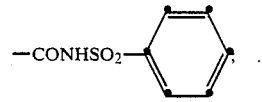

R$^4$ is a hydrogen atom or a methyl group;
R$^5$ and R$^6$ are hydogen atoms; and
Ar is phenyl substituted by fluoro or chloro; and complexes (e.g. cyclodextrin complexes) thereof.

Compounds of this type in which the carbon atom carrying the —(CH$_2$)$_n$X(CH$_2$)$_m$Z group is in the R-configuration are particularly preferred. Compounds of this type in which X is cis —CH=CH— and n is 1 and m is 3 or n is 2 and m is 2 or 4, especially where n is 1 and m is 3 or n is 2 and m is 2, are also particularly preferred.

Compounds of formula (1) inhibit gastric acid secretion, as determined for example by their ability to inhibit histamine-induced secretory responses in the rat perfused stomach, following the method of Ghosh and Schild in Br. J. Pharmacol., 1958, 13, 54 as modified by Parsons M. E., Ph.D Thesis, University of London, 1969.

The compounds also provide gastrointestinal cytoprotection, as determined for example by their ability to inhibit ethanol-induced lesions in the conscious rat, following the method of Robert et al in Gastroenterology, 1979, 77, 433, modified by the use of 5 mg/kg/s.c. indomethacin prior to the administration of the test compound.

Compounds of the invention are also able to lower lipid levels as may be demonstrated in standard animal models for example by determining their ability to lower non-esterified fatty acid levels in the starved rat (P. P. Lovisolo et. al., *Pharmacological Research Communications*, 1981, 13, 163–174; E. Schillinger and O. Loge, *Biochemical Pharmacology*, 1974, 23, 2283–2289).

The compounds are thus of interest in the prevention and/or treatment of ulcers. They may also be used in the treatment of other conditions which arise from the hypersecretion of gastric acid. They may also be used for the prevention and/or treatment of conditions in which the underlying aetiology is associated with lipid imbalance or hyperlipidemia.

According to a further aspect of the present invention we therefore provide a compound of formula (1) or a physiologically acceptable complex (e.g. cyclodextrin complex) thereof for use in the prevention and/or treatment of ulcers and other conditions arising from hypersecretion of gastric acid. We also provide a compound of formula (1) or a physiologically acceptable complex (e.g. cyclodextrin complex) thereof for use in the prevention and/or treatment of conditions in which the underlying aetiology is associated with lipid imbalance or hyperlipidemia.

According to another aspect of the invention we provide a method of treating the human or non-human animal body to combat ulcers and other conditions arising from hypersecretion of gastric acid or conditions in which the underlying aetiology is associated with lipid imbalance or hyperlipidemia, which method comprises administering to the said body an effective amount of a compound of formula (1) or a physiologically acceptable complex (e.g. cyclodextrin complex) thereof.

It will be appreciated that the compounds according to the invention may advantageously be used in conjunction with one or more other therapeutic agents, such as non-steroidal anti-inflammatory agents, or different anti-ulcer agents. It is to be understood that the present invention covers the use of a compound of formula (1) or a physiologically acceptable complex (e.g. cyclodextrin complex) in combination with one or more other terapeutic agents.

In a further aspect of the present invention we provide a pharmaceutical composition comprising as an active ingredient a compound of formula (1) or a physiologically acceptable complex (e.g. cyclodextrin complex) thereof together with one or more pharmaceutical carriers or excipients.

Compounds may be formulated in conventional manner with one or more pharmaceutical carriers, for example for oral, buccal, parenteral or rectal administration.

The compounds may be formulated for oral administration as, for example, tablets, capsules, powders, solutions or syrups prepared by conventional means with acceptable excipients.

The compounds may be formulated for parenteral administration by bolus injections or continuous infusion. Formulations for injections may be presented in unit dosage form in ampoules, or in multi-dose containers, with an added preservative.

For buccal administration, the compounds may be formulated as tablets or lozenges in conventional manner; and for rectal administration compositions such as suppositiories or retention enemas, for example containing conventional suppositiory bases such as cocoa butter or other glyceride, can be used.

The compounds are preferably administered orally, for example in amounts of 0.5 to 300 $\mu$g/kg body weight, 1 to 4 times daily. For parenteral administration, the compounds may be administered in amounts of 0.01 to 10 $\mu$g/kg body weight, 1 to 4 times daily. The precise dose will of course depend on the age and condition of the patient.

Suitable methods for preparing the compounds of the invention are described below, the various groups and symbols being as defined above except where otherwise indicated. (a) Compounds of formula (1) may be prepared by deprotection of a compound of formula (2)

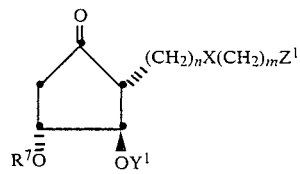

(2)

in which $Y^1$ is defined as a group

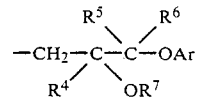

and $Z^1$ is as defined for Z in formula (1) or is a group —$CH_2OR^7$, and $R^7$ is a suitable hydroxyl protecting group [e.g.tetrahydropyran-2-yl, tetrahydrofuran2-yl, ethoxyethyl, tri(hydrocarbyl) silyl or arylmethyl].

The $R^7$ groups in the compounds of formula (2) are conveniently the same, but they may be different if desired.

Where $R^7$ is tri(hydrocarbyl)silyl the hydrocarbyl substituents may be the same or different e.g. $C_{1-6}$ alkyl, $C_{2-6}$ alkenyl, $C_{3-7}$ cycloalkyl, $C_{7-20}$ aralkyl and $C_{6-20}$ aryl groups. Such groups include methyl, ethyl, n-propyl, isopropyl, n-butyl, isobutyl, t-butyl, allyl, phenyl and benzyl. Preferred hydrocarbyl groups are $C_{1-4}$ alkyl, e.g. methyl and t-butyl. Trimethylsilyl and t-butyldimethylsilyl groups are particularly preferred.

When $R^7$ is an arylmethyl group it may contain up to 20 carbon atoms, e.g. benzyl, diphenylmethyl or triphenylmethyl.

The method used to deprotect the protected hydroxyl group will depend on the nature of $R^7$ but in general acid hydrolysis or reduction may be used.

Thus, for example when $R^7$ is a tetrahydropyran-2-yl, tetrahydrofuran-2-yl or ethoxyethyl group deprotection may be carried out with an acid. Suitable acids include inorganic acids such as hydrochloric acid and organic acids such as acetic acid or trifluoroacetic acid. Suitable solvents include ethers (e.g.diethyl ether, dioxan and tetrahydrofuran), halogenated hydrocarbons (e.g. dichloromethane), hydrocarbons (e.g. toluene), dipolar aprotic solvents (e.g. acetone, acetonitrile, dimethylsulphoxide and dimethylformamide) and alcohols (e.g. methanol, ethanol and ethylene gylcol). Where desired the solvents may be used in combination with water. The reaction may be carried out at any suitable temperature, such as from 0° to 50° C., e.g. 40° to 50° C.

A tri(hydrocarbyl)silyl group may for example be removed by acid hydrolysis, e.g. with dilute mineral acid or trifluoroacetic acid or by treatment with fluoride ions (e.g. from a quaternary ammonium fluoride such as tetra-n-butyl ammonium fluoride), or by treatment with aqueous hydrogen fluoride. Arylmethyl groups may be removed by reduction, e.g. by hydrogenolysis, e.g. with a noble metal catalyst such as platinum or palladium, or by treatment with a Lewis acid (e.g. bonron trifluoride-etherate) in the presence of a thiol (e.g. ethanethiol) in a suitable solvent such as dichloromethane at e.g. room temperature.

Compounds of formula (2) may be prepared by oxidation of a compound of formula (3)

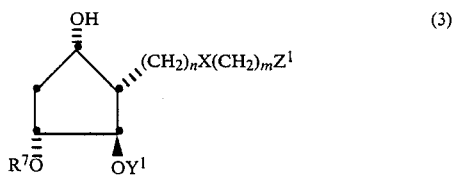

(where $Y^1$, $Z^1$ and $R^7$ are as defined just above) with for example pyridinium chlorochromate in the presence of a buffer (e.g. sodium acetate) in a suitable solvent (e.g. dichloromethane) at an appropriate temperature (e.g. $-10°$ C. to room temperature). Alternatively, the oxidation may be carried out with dimethylsulphoxide, activated by N,N'-dicyclohexylcarbodiimide, in the presence of pyridinium trifluoroacetate in a solvent such as dichloromethane at e.g. $-10°$ C. to room temperature. Other conventional oxidative methods can also be used, for example Jones reagent.

In this reaction the group $Z^1$ is other than a —CHO group. When the group $Z^1$ is —CH$_2$OH, the —OH group will need to be protected in this reaction and may be for example a group —CH$_2$OR$^7$ described above.

It wil be appreciated that the deprotection method (a) is usually applied in connection with the formation by oxidation of the cyclopentyl ring oxo group. Thus, the compounds of formula (1) may generally be prepared by oxidising a corresponding compound of formula (3) and removing the protecting groups thereafter.

Compounds of formula (2) in which $Z^1$ is —CHO may be prepared by oxidising a corresponding compound in which $Z^1$ is —CH$_2$OH using for example an activated sulphur reagent e.g. a N-chlorosuccinimide dimethylsulphide complex in a suitable solvent (e.g. toluene or dichloromethane) at temperatures of for example $-25°$ to $+25°$ C. or pyridine—SO$_3$ complex in dimethylsulphoxide, preferably at 0° C. to room temperature.

Intermediate compounds of formula (3) in which $Z^1$ is —CONHSO$_2$R$^3$ may be prepared by reacting a lactol of formula (4)

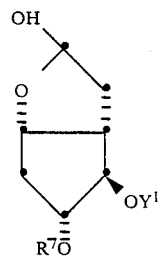

with an appropriate Wittig reagent $(R^8)_3P=CH(CH_2)_m CONHSO_2R^3$ (where $R^8$ is $C_{1-6}$ alkyl or aryl, e.g. monocyclic aryl such as phenyl) or a salt thereof, e.g. the potassium salt. Suitable solvents include hydrocarbons (e.g. benzene and toluene), ethers (e.g. tetrahydrofuran) and dialkylsulphoxides (e.g. dimethylsulphoxide). The reaction may be carried out at any suitable temperature from $-70°$ C. to 50° C., preferably at room temperature.

Lactols of formula (4) may be prepared as described in European Patent Specification No. 160495.

Intermediates of formula (3) in which $Z^1$ is —CONHR$^1$ may be prepared from a corresponding acid or ester (e.g. a compound of formula (3) in which $Z^1$ is —CO$_2$R where R is a hydrogen atom or $C_{1-6}$ alkyl) by the methods described in process (b) below. Intermediates of formula (3) in which $Z^1$ is —CH$_2$OH may also be prepared by reduction of a corresponding ester (e.g. a compound of formula (3) in which Z is —CO$_2$R where R is $C_{1-6}$ alkyl) with a reducing agent such as a complex metal hydride e.g. lithium aluminium hydride, in a suitable solvent e.g. an ether such as tetrahydrofuran at e.g. 0° C. The starting materials for this reaction may be prepared as described in European Patent Specification No. 160495. (b) Compounds of formula (1) in which Z is —CONHR$^1$ may also be prepared by amidation of the parent carboxylic acids or esters of formula (1), i.e. the corresponding compounds of formula (1) in which Z is —CO$_2$R (where R is a hydrogen atom or a $C_{1-6}$ aklyl group) or the corresponding compounds in which one or more of the hydroxyl groups present is protected, followed, if necessary, by removal of any protecting groups present.

Conventional methods for converting acids and esters into amides may be used. For example, a reactive derivative of the carboxylic acid may be treated with a compound R$^1$NH$_2$ in a suitable solvent, e.g. acetone or acetonitrile. The reactive derivative is conveniently a mixed anhydride of the acid, formed by example by treatment of the acid with a chloroformate in the presence of a suitable base, e.g. triethylamine or pyridine.

The chloroformate may for example be a $C_{1-6}$ alkyl (e.g. isobutyl), aryl (e.g. phenyl) or aralkyl (e.g. benzyl) chloroformate.

Alternatively, the reactive derivative may be an imidazolide, formed for example by treatment of the acid with 1,1'-carbonyldiimidazole.

Conventional methods of protection and deprotection may be used, as described above in process (a).

The parent carboxylic acids and esters required as starting materials in this process may be prepared by the methods described in European Patent Specification No. 160495. (c) Compounds of formula (1) in which X is a —CH$_2$—CH$_2$— group may be prepared by reduction of a corresponding compound of formula (1) in which X is a cis or trans —CH=CH— group or an acetylene group. Suitable methods of reduction include hydrogen in the presence of a catalyst, e.g. palladium, on a support (e.g. carbon). Suitable solvents include ethyl acetate, ethanol and methanol. (d) Compounds of formula (1) in which X is a —CH═CH— group may be prepared by reduction of a corresponding compound of formula (1) in which X is an acetylene group. Suitable methods of reduction include hydrogen in the presence of a catalyst, e.g. palladium on a support (e.g. $CaCO_3$ or $BaSO_4$) and poisoned for example by lead or quinoline. Suitable solvents include ethyl acetate and methanol. This reaction is particularly suitable for the preparation of compounds of formula (1) in which X is cis —CH═CH—.

The acetylenes required as starting materials in this process may be prepared from the corresponding acetylenic acids using the methods described above. The acetylenic acid intermediates may be prepared by the methods generally described in European Patent Specification No. 160495. (e) Compounds of formula (1) in which X is a trans —CH═CH— group may be prepared by isomerisation of a corresponding compound of formula (1) in which X is a cis —CH═CH— group. The isomerisation may for example be effected by treating the corresponding cis compound with toluene-p-sulphinic acid in dioxan (e.g. at reflux), or azobisisobutyronitrile and thiophenol, using for example a hydrocarbon solvent (e.g. benzene) at any suitable temperature up to reflux.

Complexes (e.g. cyclodextrin complexes) may be prepared using conventional methods e.g. by treating a compound of formula (1) with α-, β- γ-cyclodextrin in a suitable solvent.

The processes in methods (b)–(e) may also be applied to compounds of formula (2), or in particular compounds of formula (3), and the products subsequently converted into compounds of formula (1) by the methods described above.

When a specific enantiomer of formula (1) is required, starting materials having the desired stereochemical configuration should be used in the above processes. Such starting materials may be prepared for example using the methods described in European Patent Specification No. 160495 from an enantiomeric intermediate as described in European Patent Specification No. 74856.

The following examples illustrate the invention. Temperatures are in °C. 'Dried' refers to drying with anhydrous $MgSO_4$. T.l.c. - Thin layer chromatography on silica. Chromatography was carried out on silica gel. The following abbreviations are used:

ER-ether; EA-ethyl acetate; PE-petroleum ether (b.p. 40°–60° unless otherwise stated); THF-tetrahydrofuran; $CH_2Cl_2$-dichloromethane; $CHBr_3$-bromoform; DMSO-dimethylsulphoxide; MeOH-methanol; $Et_3N$-triethylamine; $LiAlH_4$-lithium aluminium hydride; NaOH-sodium hydroxide; $CHCl_3$-chloroform.

INTERMEDIATE 1

[1S-[1α(Z), 2β(2S*), 3α, 5α]]-Methyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate

INTERMEDIATE 2

(2a) [3aR-(3aα, 4α(2R*), 5β, 6aα])-(−)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-ol (2b) [3aR-(3aα, 4α, 5β, 6aα])-(−)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-ol Intermediates 1 and 2 are prepared as described in European Patent Specification No. 160495.

INTERMEDIATE 3

(3a) [1S-[1α, 2α(Z), 3β(2S*), 4α]]-(+)-2-(7-Hydroxy-2-heptenyl)-3-[3-phenoxy-2-[(tetrahydro-2H-pyran-2-yl)oxy]propoxy[-4-[(tetrahydro-2H-pyran-2-yl)oxy]cyclopentanol A solution of Intermediate 1 (0.44 g) in ER (10 ml) was added to a slurry of $LiAlH_4$ (0.080 g) in ER (5 ml) at 0°–5°. The mixture was stirred at ambient temperature for 4h. Water (0.04 ml) was added followed by 2N NaOH (0.1 ml) and water (0.1 ml). The mixture was filtered through hyflo and the filtrate was evaporated in vacuo. The residue was purified by chromatography using ER as eluant to give the title compound as a colourless oil (0.4 g). I.r. ($CHBr_3$) 3610, 3520 $cm^{-1}$. $[α]D^{20}+16.9°$ (MeOH).

(3b) [1S-[1α(Z), 2β(2S*), 3α, 5α]]-(+)-7-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenamide A solution of Intermediate 1 (0.7 g) in saturated methanolic ammonia (25 ml) was kept at 23° for 3 weeks. The solution was evaporated and the residue purified by chromatography using EA as eluant to give the title compound as an oil (0.63 g). I.r. ($CHBr_3$) 3520, 3400, 1670, 1595 $cm^{-1}$. $[α]^{20}D+36.5°$ ($CHCl_3$).

(3c) [1S-[1α(Z), 2β(2S*), 3α, 5α]]-N-Acetyl-7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenamide A mixture of 50% sodium hydride in mineral oil (0.16 g), dry DMF (4 ml) and acetamide (0.7 g) was heated at 75° under nitrogen for 0.5h. A solution of Intermediate 1 (0.5 g) in dry DMF (3 ml) was added and the mixture was stirred at 70° for 0.5h. The cooled mixture was diluted with phosphate buffer (pH 6.5, 25 ml) and extracted with ER (2×25 ml), brine (25 ml), dried and evaporated in vacuo. Purification of the residue by chromatography using EA-cyclohexane (7:3) gave the title compound as an oil (0.27 g). I.r. ($CHBr_3$) 3520, 3390, 1730, 1700 $cm^{-1}$.

(3d) [1S-[1α, 2α(Z), 3β(2S*), 4α]]-3-[3-Phenoxy-2-[(tetrahydro-2H-pyran-2-yl)oxy]propoxy]-4-[(tetrahydro-2H-pyran-2-yl)oxy]-2-[7-[(tetrahydro-2H-pyran-2-yl)oxy]-2-heptenyl]cyclopentanol A mixture of Intermediate 3a (62 mg), pyridinium p-toluenesulphonate (6 mg) and dihydropyran (0.01 ml) in $CH_2Cl_2$ was stirred at ambient temperature for 2.5h. The mixture was washed with water (10 ml) and 8% sodium bicarbonate (10 ml), and then dried. Removal of the solvent gave a residue which was purified by chromatography using EA-PE (3:2) as eluant to give the title compound as an oil (28 mg). I.r. (CHBr$_3$) 3530 cm$^{-1}$.

(3e) [1S-[1α(Z), 2β(2S*), 3α, 5α]-(+)-7-[5-Hydroxy-2-[3-phenoxy-2-[(tetrahydro-2H-pyran-2-yl)oxy]propoxy]-N-(methylsulphonyl)-3-[(tetrahydro-2H-pyran-2-yl)oxy]cyclopentyl]-5-heptenamide A solution of Intermediate 5a (2.4 g) in THF (40 ml) was treated with potassium t-butoxide (1.0 g) and the mixture was stirred at ambient temperature for 2h. A solution of Intermediate 2a in THF (10 ml) was added and the mixture was stirred for 1h. Saturated ammonium chloride (20 ml) was added and the organic solvent was removed in vacuo. The residue was extracted with EA (3×50 ml) and the combined extracts were washed with brine (20 ml), dried and evaporated. Purification by chromatography using EA-CHCl$_3$ (1:1) as eluant gave the title compound as an oil. (0.33 g). I.r. (CHBr$_3$) 1710 cm$^{-1}$. [α]$^{20}$D+14.2° (MeOH).

The following compound was prepared in a similar manner to Intermediate 3e.

(3f) [1S-[1α(Z), 2,β, 3α, 5α]]-(+)-7-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]-N-(phenylsulphonyl)-5-heptenamide.

I.r. (CHBr$_3$) 3600–3400, 1720 cm$^{-1}$. [α]D$^{20}$+16.5° (MEOH).

From Intermediates 2b and 5b.

INTERMEDIATE 4

(4a) [2R-[2α(Z), 3β, (2R*), 4α]]-3-[3-Phenoxy-2-[(tetrahydro-2H-pyran-2-yl)oxy]propoxy]-4-[(tetrahydro-2H-pyran-2-yl)oxy]-2-[7-[(tetrahydro-2H-pyran-2-yl)oxy]-2-heptenyl]cyclopentanone A solution of Intermediate 1d (0.2 g) and N,N$^1$-dicyclohexylcarbodiimide (0.25 g) in a mixture of DMSO (0.25 ml) and CH$_2$Cl$_2$ (3 ml) at ambient temperature was treated with pyridinium trifluoroacetate (0.12 g). The mixture was stirred at ambient temperature for 2.5h. Water (10 ml) was added and the product was extracted with ER (2×20 ml). The extract was dried and evaporated leaving a residue which was purified by chromatography on acid-washed silica (pH 3.8) using ER-PE (5:3) as eluant to give the title compound as an oil (0.14 g). I.r. (CHBr$_3$) 1740 cm$^{-1}$.

(4b) [1R-[1α(Z), 2β(2R*), 3α]]-7-[5-Oxo-2[3-phenoxy-2-[(tetrahydro-2H-pyran-2-yl)oxy]propoxy]-3-[(tetrahydro-2H-pyran-2-yl)oxy]cyclopentyl]-5-heptenamide Pyridinium chlorochromate (0.63 g) was added to a stirred suspension of Intermediate 3b (0.55 g) and anhydrous sodium acetate (0.47 g) in dry CH$_2$Cl$_2$ (25 ml) at 0°. The mixture was stirred at 0° for 3h, diluted with EA (30 ml) and filtered through a small wad of acid-washed silica (pH 3.8). The combined filtrates were washed consecutively with 10% aqueous copper sulphate (2×50 ml), water (50 ml) and brine (50 ml). Drying and evaporation in vacuo gave the title compound as an oil (0.38 g). I.r. (CHBr$_3$) 3520, 3400, 1740, 1675 cm$^{-1}$.

The following compound was prepared in a similar manner to Intermediate 4b.

(4c) [1R-[1α(Z), 2β(2R*), 3α]]-N-Acetyl-7-[5-oxo-2-[3-phenoxy-2-[(tetrahydro-2H-pyran-2-yl)oxy]propoxy]-3-[(tetrahydro-2H-pryan-2-yl)oxy]cyclopentyl]-5-heptenamide (0.12 g) as an oil. I.r. (CHBr$_3$) 3380, 1738, 1700 cm$^{-1}$ From Intermediate 3c (0.24 g) except that the crude product was purified by chromatography on acid-washed silica (pH 3.8) using EA-cyclohexane (1:1) as eluant.

The following compounds were prepared in a similar manner to Intermediate 4c.

(4d) [1R-[1α(Z), 2β(2R*), 3α]]-(−)-N-(Methylsulphonyl)-7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenamide I.r. (CHBr$_3$) 3360, 1738, 1720 cm$^{-1}$. [α]$^{21}$D−10° (MeOH)

From Intermediate 3e.

(4e) [1R-[1α(Z), 2β, 3α]]-7-[5-Oxo-2-[3-phenoxy-2-[(tetrahydro-2H-pyran-2-yl)oxy]propoxy]-3-[(tetrahydro-2H-pyran-2-yl)oxy]cyclopentyl-N-(phenylsulphonyl)-5-heptenamide I.r. (CHBr$_3$) 1725 cm$^{-1}$ From Intermediate 3f.

INTERMEDIATE 5

(5a) [5-[(Methylsulphonyl)amino]-5-oxopentyl]triphenylphosphonium bromide

(5b) [5-Oxo-5-[(phenylsulphonyl)amino]pentyl]triphenylphosphonium bromide

The above intermediates were prepared by the literature procedures described in J. Med. Chem., 1979, 22, 1340.

EXAMPLE 1

[2R-[2α(Z), 3β(R*), 4α]]-4-Hydroxy-2-(7-hydroxy-2-heptenyl)-3-(2-hydroxy-3-phenoxypropoxy)cyclopentanone A solution of Intermediate 4a (0.14 g) in acetic acid-water-THF (20:10:3, 2 ml) was heated at 40° for 4h. The solvent was removed in vacuo and the residue purified by chromatography on acid-washed (pH 3.8) silica using ER-MeOH (70:1) as eluant to give the title compound as an oil (0.04 g). I.r. (CHBr$_3$) 3600, 3450, 1748 cm$^{-1}$.

Analysis Found C, 66.80; H, 8.07; $C_{21}H_{30}O_6$ requires C, 66.64; H, 7.99%.

In a similar manner were prepared the following compounds.

EXAMPLE 2

[1R-[1α(Z), 2β(R*), 3α]]-(−)-7-[3-Hydroxy-2-(2-hydroxy-3-phenoxy-propoxy)-5-oxocyclopentyl]-5-heptenamide as an oil (0.95 g). I.r. (CHBr₃) 3585, 3520, 3400, 1740, 1672, 1598, 1588 cm⁻¹. T.l.c. (EA-MeOH, 95:5) Rf 0.38.

From Intermediate 4b (0.35 g) except that EA-MeOH (95:5) was used as eluant.

EXAMPLE 3

[1R-[1α(Z), 2β(R*), 3α]]-N-Acetyl-7-[3-hydroxy-2-(2-hydroxy-3-phenoxy-propoxy)-5-oxocyclopentyl]-5-heptenamide as an oil (0.034 g)

I.r. (CHBr₃) 3580, 3380, 1740, 1700 cm⁻¹. Analysis Found C, 63.3; H, 7.3; N, 3.6. $C_{23}H_{31}NO$, requires C, 63.7; H, 7.2; N, 3.2%.

From Intermediate 4c (0.1 g) except that EA was used as eluant.

EXAMPLE 4

[1R-[1α(Z), 2β(R*), 3α]]-(−)-7-[3-Hydroxy-2-(2-hydroxy-3-phenoxy-propoxy)-5-oxocyclopentyl]-N-(methylsulphonyl)-5-heptenamide as an oil (0.13 g). I.r. (CHBr₃) 3580, 3360, 1740, 1715 cm⁻¹. T.l.c. (CHCl₃-MeOH, 19:1) Rf 0.2. $[\alpha]^{21}_D -8°$ (MeOH).

From Intermediate 4d (0.18 g) except that CHCl₃-MeOH (19:1) was used as eluant.

EXAMPLE 5

[1R-[1α(Z), 2β, 3α]]-(−)-7-[3-Hydroxy-2-(2-hydroxy-3-phenoxy-propoxy)-5-oxocyclopentyl]-N-(phenylsulphonyl)-5-heptenamide as an oil (0.075 g), I.r. (CHBr₃) 3590, 3370, 1740, 1725 cm⁻¹. T.l.c. (EA-PE, 3:1) Rf 0.22. $[\alpha]^{20}_D -15.2°$ (MeOH)

From Intermediate 4e (0.17 g) except that EA-PE (3:1) was used as eluant.

The following are examples of pharmaceutical formulations using compounds of the invention. In the examples, the term "active ingredient" is used to denote a compound of the invention, such as a compound described in the preceding examples.

| 1. Tablets | mg/tablet |
|---|---|
| *These may be prepared by direct compression* | |
| Active Ingredient | 0.015 to 0.2 |
| Magnesium stearate, BP | 1.5 |
| Microcrystalline cellulose, USP | 150.0 |
| to compression weight | |

The active ingredient is blended with about 10% of the microcrystalline cellulose then blended with the remaining microcrystalline cellulose and magnesium stearate. The blend is then compressed using 6 mm diameter punches into tablets on a suitable machine.

The tablets may be film coated with suitable film forming materials e.g. methyl cellulose or hydroxypropyl methylcellulose using standard techniques.

| 2. Capsules | mg/tablet |
|---|---|
| Active ingredient | 0.015 to 0.2 |
| Magnesium stearate, BP | 1.0 |

| 2. Capsules | mg/tablet |
|---|---|
| *Starch 1500 | 100.0 |
| to fill weight | |

*A form of directly compressible starch.

The active ingredient is preblended with some of the Starch 1500 then this preblend is mixed with the remaining Starch 1500 and magnesium stearate. The mix is then filled into size No 2 hard gelatin capsule shells using suitable machinery.

We claim:

1. Compounds of the general formula (1)

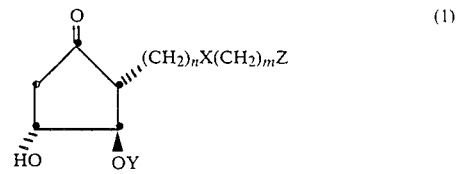

wherein
n is 1 or 2;
m is 2-5 and X is cis or trans —CH=CH— or —CH₂—CH₂—; or m is 1-4 and X is —CH=C=CH—;
Z is —CH₂OH, —CHO or —CONHR¹ where R¹ is a hydrogen atom or $C_{1-4}$ alkyl, aryl, —COR² (where R² is a hydrogen or a $C_{1-4}$ alkyl or aryl group) or —SO₂R³ (where R³ is a $C_{1-4}$ alkyl or aryl group);

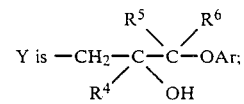

where R⁴, R⁵ and R⁶ is each a hydrogen atom or a methyl group and at least one is a hydrogen atom; and
Ar is a phenyl group, or a phenyl group substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups; or complexes thereof.

2. Compounds as claimed in claim 1 in which X is —CH=CH— or —CH₂—CH₂— and m is 3 when n is 1 and m is 2 or 4 when n is 2; or X is —CH=C=CH— and m is 2 when n is 1 and m is 1 or 3 when n is 2.

3. Compounds as claimed in claim 1 in which Z is —CH₂OH, —CHO, —CONH₂, —CONHCH₃, —CONHCOCH₃, —CONHSO₂CH₃ or

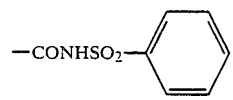

4. Compounds as claimed in claim 1 in which R⁵ and R⁶ are hydrogen atoms and Ar is phenyl or phenyl substituted by fluoro or chloro.

5. Compounds as claimed in claim 1 in which:
X is —CH=CH— or —CH₂—CH₂— and n is 1 and m is 3 or n is 2 and m is 2 or 4, or X is —CH=C=CH— and n is 1 and m is 2 or n is 2 and m is 1 or 3;
Z is —CH₂OH, —CHO, —CONH₂, —CONHCH₃, —CONHCOCH₃, —CONHSO₂CH₃ or

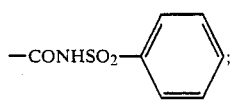

$R^4$ is a hydrogen atom or a methyl group;

$R^5$ and $R^6$ are hydrogen atoms; and

Ar is phenyl or phenyl substituted by fluoro or chloro; and complexes thereof.

6. Compounds as claimed in claim 5 in which X is cis —CH=CH—.

7. Compounds as claimed in claim 5 in which X is cis —CH=CH—, and n is 1 and m is 3 or n is 2 and m is 2.

8. Compounds as claimed in claim 1 in which the carbon atom carrying the group —$(CH_2)_nX(CH_2)_mZ$ is in the R-configuration.

9. A pharmaceutical composition comprising a compound as claimed in claim 1 together with one or more pharmaceutical carriers.

10. A process for the preparation of a compound as claimed in claim 1 which comprises:

(a) deprotecting a compound of formula (2)

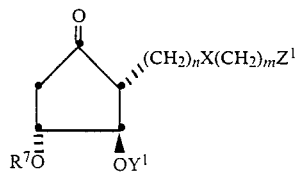

(2)

in which $Y^1$ is defined as a group $$-CH_2-\underset{R^4}{\underset{|}{C}}-\underset{OR^7}{\underset{|}{C}}-OAr$$
$$\phantom{-CH_2-}R^5\phantom{xx}R^6$$

and $Z^1$ is as defined for Z in formula (1) or is a group —$CH_2OR^7$, and $R^7$ is a hydroxyl protecting group;

(b) in the preparation of a compound in which Z is —$CONHR^1$, amidating a corresponding compound of formula (1) in which Z is —$CO_2R$ (where R is a hydrogen atom or a $C_{1-6}$ alkyl group) or the corresponding compounds in which one or more of the hydroxyl groups present is protected, followed, if necessary, by removal of any protecting groups present;

(c) in the preparation of a compound in which X is —$CH_2$—$CH_2$—, reducing a corresponding compound in which X is —CH=CH— or an acetylene group;

(d) in the preparation of a compound in which X is —CH=CH—, selectively reducing the corresponding compound in which X is an acetylene group;

(e) in the preparation of a compound in which X is trans —CH=CH—, isomerising the corresponding compound in which X is cis —CH=CH—; or (f) treating a compound of formula (1) with cyclodextrin to form a complex.

* * * * *